United States Patent [19]

Lee et al.

[11] Patent Number: 5,198,595

[45] Date of Patent: Mar. 30, 1993

[54] ALKYLATION OF AROMATIC COMPOUNDS

[75] Inventors: Guo-shuh J. Lee; Juan M. Garces, both of Midland, Mich.; Garmt R. Meima; Matheus J. M. van der Aalst, both of Terneuzen, Netherlands

[73] Assignee: The Dow Chemical Company, Midland, Mich.

[21] Appl. No.: 718,741

[22] Filed: Jun. 21, 1991

Related U.S. Application Data

[60] Continuation-in-part of Ser. No. 455,677, Dec. 22, 1989, and a continuation-in-part of Ser. No. 699,441, Apr. 22, 1991, which is a continuation-in-part of Ser. No. 422,187, Oct. 16, 1989, abandoned, which is a division of Ser. No. 323,530, Mar. 14, 1989, Pat. No. 5,004,841, which is a continuation-in-part of Ser. No. 123,741, Nov. 23, 1987, Pat. No. 4,891,448, and Ser. No. 455,677, Nov. 23, 1987, which is a continuation-in-part of Ser. No. 323,530, Mar. 14, 1989, Pat. No. 5,004,841, which is a continuation-in-part of Ser. No. 123,741, Nov. 23, 1987, Pat. No. 4,891,448.

[51] Int. Cl.$^5$ .......................... C07C 2/66; C07C 37/48; C07C 209/68

[52] U.S. Cl. ............................... 585/467; 585/449; 585/452; 585/475; 568/791; 568/794; 564/409

[58] Field of Search ............... 568/794, 791; 585/470, 585/475, 467, 449, 452; 502/64; 564/409

[56] References Cited

U.S. PATENT DOCUMENTS

| | | |
|---|---|---|
| 2,431,166 | 4/1943 | Buell et al. ........................ 568/794 |
| 3,140,253 | 5/1964 | Plank et al. . |
| 3,251,897 | 5/1966 | Wise .................................... 260/120 |
| 3,367,884 | 2/1968 | Reid et al. . |
| 3,480,539 | 10/1968 | Voorhies et al. . |
| 3,485,748 | 12/1968 | Eberly et al. . |
| 3,551,510 | 8/1968 | Pollitzer et al. . |
| 3,562,345 | 2/1971 | Mitsche . |
| 3,597,155 | 8/1971 | Flannigan et al. . |
| 3,597,493 | 8/1971 | Frilette et al. . |
| 3,631,120 | 12/1971 | Eberly et al. . |
| 3,641,177 | 2/1972 | Eberly et al. . |
| 3,699,181 | 10/1972 | Kamecak et al. .................. 260/672 |
| 3,716,597 | 2/1973 | Mitsche et al. . |
| 3,719,026 | 3/1973 | Sand . |
| 3,758,667 | 9/1973 | Kouwenhoven et al. . |
| 3,763,260 | 10/1973 | Pollitzer . |
| 3,849,340 | 11/1974 | Pollitzer . |
| 3,873,632 | 3/1975 | Pollitzer ............................ 260/668 |
| 3,972,832 | 8/1976 | Butter et al. . |
| 4,085,156 | 4/1978 | Filette et al. . |
| 4,108,908 | 8/1978 | Rutledge ............................ 568/730 |
| 4,151,120 | 8/1979 | Marcilly . |
| 4,169,111 | 9/1979 | Wight ............................ 585/455 Z |
| 4,180,693 | 12/1979 | Marcilly ............................ 585/475 |
| 4,182,692 | 1/1980 | Kovosky et al. .................. 252/455 |
| 4,185,040 | 1/1980 | Ward et al. ........................ 585/467 |
| 4,240,932 | 12/1980 | Alafandi et al. .................. 252/455 |
| 4,263,466 | 4/1981 | Colon et al. ...................... 585/421 |
| 4,283,573 | 8/1981 | Young . |
| 4,301,317 | 11/1981 | Young ................................ 585/455 |
| 4,323,481 | 4/1982 | Kaduk ............................ 252/455 Z |
| 4,361,713 | 11/1982 | Kaeding ............................ 585/467 |
| 4,371,714 | 2/1983 | Young ................................ 568/62 B |
| 4,376,104 | 3/1983 | Ball et al. .......................... 423/329 |
| 4,420,418 | 12/1983 | Chu .................................... 502/77 |
| 4,447,669 | 5/1984 | Hamon et al. .................... 585/640 |
| 4,459,426 | 7/1984 | Inwood et al. .................... 585/323 |
| 4,480,142 | 10/1984 | Cobb .................................. 585/465 |
| 4,501,656 | 2/1985 | Dufresne et al. . |
| 4,525,466 | 6/1985 | Moretti et al. .................... 502/63 |
| 4,665,258 | 5/1987 | Butler et al. ...................... 585/475 |
| 4,731,497 | 3/1988 | Grey .................................. 585/455 |
| 4,745,095 | 5/1988 | Saito et al. . |
| 4,774,377 | 9/1988 | Barger et al. ...................... 585/323 |
| 4,849,570 | 7/1989 | Bakas et al. ...................... 585/467 |
| 4,857,666 | 8/1989 | Barger et al. ...................... 585/323 |

FOREIGN PATENT DOCUMENTS

| | | |
|---|---|---|
| 0202752 | 11/1985 | European Pat. Off. . |
| 0285280 | 3/1987 | European Pat. Off. . |
| 366515 | 5/1990 | European Pat. Off. . |
| 2084704 | 12/1971 | France . |
| 56-133224 | 10/1981 | Japan . |
| 56-156222 | 12/1981 | Japan . |
| 58-159427 | 9/1983 | Japan . |
| 63-8803523 | 3/1988 | Japan . |
| 63-122635 | 5/1988 | Japan . |
| 1-190639 | 7/1989 | Japan . |
| 90/03961 | 4/1990 | PCT Int'l Appl. . |

OTHER PUBLICATIONS

*Studies in Surface Science and Catalysis*, V18, (1984), pp. 133–140; H. K. Beyer et al. Structural Peculiarities and Stabilsation phenomena of Aluminum Deficient Mordenites.

*Zeolites*, V7, (1987), pp. 427–433, M. Musa, et al.; Some structural characteristics of dealuminated sythetic mordenites.

*Derwent*, 84–141746/23JP, (1982).

*Derwent;* 78145 D/43 FR, (1980).

(List continued on next page.)

*Primary Examiner*—Marianne M. Cintins
*Assistant Examiner*—Margaret J. Page

[57] ABSTRACT

Monoalkylated benzene such as ethylbenzene and cumene or monoalkylated substituted benzene are produced by alkylation in the presence of an acidic mordenite zeolite catalyst having a silica/alumina molar ratio of at least 40:1, preferably 160:1. In a subsequent, optional process, the polyalkylated benzene or polyalkylated substituted benzene produced in the alkylation is transalkylated in the presence of an acidic mordenite zeolite catalyst.

37 Claims, No Drawings

OTHER PUBLICATIONS

*Derwent;* 76464A/43 FARF, (1976).
*Derwent,* 86–065632/10JP, (1981).
*Polish Journal of Chem.,* 60,255.(1986); B. Sulikowski et al. Effect of Dealumination on Sorption Properties of Zeolon 300, 900 and 500.
*Bulletin of the Acad. of Sciences of USSR,* #7, 1971, pp. 1298–1303, I. M. Belen'kaya et al.; Formation and Properties of the Hydrogen Form of Mordenite.
*Bulletin of the Acad. of Sciences of USSR,* #12, 1971, pp. 2505–2509, I. M. Belen'kaya et al. Formation and Properties of the Hydrogen Form of Mordenite.
*Journal of Catalysis,* 28 (1973), pp. 403–413, K. A. Becker et al.; Benzene Alkylation with Ethylene and Propylene over H–Mordenite as Catalyst.
*Kinetika i Kalatiz,* V19, No. 1, pp. 256–259, (1978), M. I. Dashevskii, et al.; Electron Microscopic Study of a Nickel–Mordenite Catalyst.
*Kirk–Othmer Encyclopedia of Chemical Technology,* 3rd Ed., vol. 14, John Wiley & Sons N.Y., N.Y., pp. 395–427.
D. W. Breck, *Zeolite Molecular Sieves,* John Wiley & Sons, (1974) pp. 122–124 and 162–163.
J. D. Sherman and J. M. Bennett, "Framework Structures Related to the Zeolite Mordenite," *Molecular Sieves,* Advances in Chemistry Series, 121 (1973), pp. 52–65.
Chemical Abstracts 82:169681b (1975).
Chemical Abstracts 82:57148b (1975).

ALKYLATION OF AROMATIC COMPOUNDS

CROSS-REFERENCE TO RELATED APPLICATIONS

This application is a continuation-in-part of co-pending application Ser. No. 455,677, filed Dec. 22, 1989 which is a continuation-in-part of co-pending application Ser. No. 323,530, filed Mar. 14, 1989, now U.S. Pat. No. 5,004,841, which is a continuation-in-part of application Ser. No. 123,741, filed Nov. 23, 1987, now U.S. Pat. No. 4,891,448. This application is also a continuation-in-part of co-pending patent application Ser. No. 422,187, filed Oct. 16, 1989, now abandoned, which is a divisional of patent application Ser. No. 323,530, filed Mar. 14, 1989, now U.S. Pat. No. 5,004,841, which is a continuation-in-part of patent application Ser. No. 123,741, filed Nov. 23, 1987, now U.S. Pat. No. 4,891,448.

BACKGROUND OF THE INVENTION

This invention relates to the use of mordenite zeolites as catalysts in the monoalkylation of aromatic compounds to produce cumene, ethylbenzene, and other alkylated benzenes.

Cumene, also known as isopropylbenzene, is useful for the production of phenol, acetone, and alphamethylstyrene. Ethylbenzene is useful in the production of styrene. Various processes for their manufacture are known.

Various processing schemes comprising alkylation and/or transalkylation are known to produce monoalkylaromatic products such as cumene or ethylbenzene in high yields. However, existing processes are not without problems including the production of undesirable by-products. Examples of such by-products produced in conjunction with cumene include alkylating agent oligomers, heavy polyaromatic compounds and unwanted monoalkylated and dialkylated compounds such as n-propylbenzene, butylbenzenes and ethylbenzene. The production of unwanted xylenes are a particular problem in the production of ethylbenzene. Another problem with existing processes concerns the use of Friedel Crafts catalysts such as solid phosphoric acid or aluminum chloride. The phosphoric acid catalysts generally require the use of a water co-feed which produces a corrosive sludge by-product. Problems concerning the sludge by-product can be avoided by the use of zeolite catalysts. However, major drawbacks of the zeolite catalyzed gas phase processes include the production of undesirable by-products and the relatively rapid deactivation of the catalyst.

It is known that aromatic hydrocarbons can be alkylated in the presence of acid-treated zeolite. U.S. Pat. No. 4,393,262 (1983) teaches that cumene is prepared by the alkylation of benzene with propylene in the presence of a specified zeolite catalyst. U.S. Pat. No. 3,140,253 (1964) and U.S. Pat. No. 3,367,884 (1968) broadly teach the use of acid-treated mordenite for the alkylation of aromatic compounds. However, such alkylations are generally not selective with respect to site and number of substitutions. Further, catalysts are often quickly deactivated requiring timely and costly replacements or reactivation.

Important criteria which determine the feasibility of a commercial process for the alkylation of benzene or substituted benzene, besides the above-mentioned criteria regarding environmental impact, low level of impurities which are difficult to remove from the process stream and/or to convert to desired products, activity and stability of the catalyst, include the following: the conversion based on the alkylating agent should be substantially 100 percent in order to prevent expensive recycling of unconverted alkylating agent or loss of alkylating agent to flare: the selectivity towards the monoalkylated benzene should be high: the recycle of benzene or substituted benzene should be minimized as it is rather expensive and leads to the larger quantities of impurities which are recycled to the alkylation reactor and passed over the catalyst. Minimizing the recycle of benzene or substituted benzene could be achieved by decreasing the molar ratio of benzene or substituted benzene to alkylating agent. However, it is known that the conventional zeolite type catalysts tend to deactivate under these conditions because of increased tendency of the alkylating agent to polymerize and because of the increased polyalkylation activity. Apart from catalyst deactivation this, moreover, would lead to a decreased selectivity towards the monoalkylated benzene. Therefore, the main object of the conventional zeolite catalyzed processes was to optimize conversion of the alkylating agent and selectivity towards the monoalkylated product in the alkylation step or process in itself.

Thus, there remains a need for an effective process for the preparation of monoalkylated benzenes having minimal levels of impurities utilizing a catalyst having low negative environmental impact and long life.

SUMMARY OF THE INVENTION

It has now been found that benzene or substituted benzene may be alkylated to form monoalkylated benzene or monoalkylated substituted benzene in the presence of an acidic mordenite zeolite having a silica/alumina molar ratio of at least 30:1, preferably of at least 160:1. Unexpectedly, the products have low levels of polyalkylated products and low levels of impurities. This process comprises contacting benzene or substituted benzene with an alkylating agent having from about two to about eighteen carbon atoms in the presence of the acidic mordenite zeolite catalyst having a silica/alumina molar ratio of at least 30:1, preferably 160:1, and a crystalline structure which is determined by X-ray diffraction to have a Symmetry Index of at least 1 under conditions such that alkylated benzene or substituted benzene having a low content of impurities is produced. A catalyst having a silica/alumina molar ratio of at least 160:1 in an alkylation reaction produces a higher selectivity and conversion toward monoalkylated products than a catalyst having a lower silica/alumina molar ratio. Likewise, the lifetime of the catalyst is longer in the alkylation reaction than that of a catalyst having lower silica/alumina molar ratios.

The polyalkylated benzene or polyalkylated substituted benzene fraction of the alkylation product can be separated from the monoalkylated benzene or monoalkylated substituted benzene from the alkylation product. The polyalkylated benzene or polyalkylated substituted benzene fraction can be contacted with benzene in a transalkylation in the presence of an acidic mordenite catalyst having a silica/alumina molar ratio of at least 50:1 under conditions sufficient for the formation of monoalkylated benzene or monoalkylated substituted benzene.

In a preferred embodiment of the present invention, alkylation followed by transalkylation provides a two catalyst bed process having a well-balanced combination of low levels of undesired by-products, a liquid phase process with relatively mild operating conditions, an active catalyst which provides a conversion of the alkylating agent of substantially 100 percent at the low benzene or substituted benzene to alkylating agent molar ratios, and a high selectivity towards monoalkylated benzene or polyalkylated substituted benzene and polyalkylated benzene or polyalkylated substituted benzene having the same alkyl substituent as in the desired monoalkylated product. The major product is the monoalkylated product, whereas the polyalkylated benzenes are primarily dialkylated benzenes which may be easily converted in an optional subsequent transalkylation. These advantages are achieved under conditions of low benzene or substituted benzene to alkylating agent ratios and substantially without increasing catalyst deactivation rate, which is very surprising in view of the prior art.

The catalyst of the present invention can be employed in alkylation and transalkylation processes which exhibit significant advantages over present day commercial alkylation and transalkylation processes. Ethylbenzene and cumene, for example, are typically manufactured in a liquid or gas phase alkylation utilizing, respectively, solid phosphoric acid or Friedel-Crafts catalysts such as aluminum chloride. Disadvantageously, these processes require handling large quantities of aluminum chloride, designing corrosion resistant equipment, and disposing of a waste alumina and salt stream. In contrast, the catalyst of this invention can be employed in the alkylation of benzene to ethylbenzene or cumene advantageously eliminating the need for aluminum chloride, special corrosion resistant equipment and disposal of a metal oxide and salt waste stream. More advantageously, the catalyst of this invention produces cumene having a low bromine index, which correlates with a desirably low level of unsaturates, and low levels of impurities such as n-propylbenzene, butylbenzene and ethylbenzenes. Under the conditions of this process, cumene is produced having unexpectedly low levels of polyalkylated products. Even more advantageously, the catalyst of this invention produces cumene which is nearly free of n-propylbenzene and o-diisopropylbenzene, typical by-products of the Friedel-Crafts or phosphoric acid route which are difficult to separate from cumene. As a further advantage, the catalyst of this invention can be employed in the alkylation of benzene with ethylene to produce ethylbenzene which is essentially free of xylenes and which has low levels of polyalkylated products. In contrast, the well-known Mobil-Badger process for manufacturing ethylbenzene produces large amounts of xylenes which are difficult to separate from ethylbenzene. In addition, the catalyst of this invention is active at temperatures lower than those typically employed in the gas phase Mobil-Badger process.

Most advantageously, the catalyst of this invention possesses a long lifetime and an unexpectedly low rate of deactivation. For this reason the catalyst of the invention is suitable for commercial application in any of the above-identified dialkylation, mono-alkylation, and transalkylation processes.

Cumene produced by the practice of this invention is useful in the production of phenol or methyl-styrene. Ethylbenzene produced is useful in the production of styrene.

DETAILED DESCRIPTION OF THE INVENTION

Any monocyclic aromatic compound may be monoalkylated by the process of this invention. The aromatic compound is preferably benzene or substituted benzene. Non-limiting examples of substituted benzenes which may be monoalkylated by the process of this invention include toluene, xylene, phenol, and aniline. More preferably, the aromatic compound is benzene.

The aromatic compound may be used neat in a liquid state, or dissolved in a suitable solvent. Preferably, the aromatic compound is used in a neat liquid state. If a solvent is employed, any inert solvent which solubilizes the aromatic compound and does not hinder the monoalkylation reaction may be used. The preferred solvent is a saturated hydrocarbon.

The alkylating agent used may be any aliphatic or cycloaliphatic olefin having from two to eighteen carbon atoms. Preferably, an aliphatic olefin having from two to twelve carbon atoms is used. In the alkylation of benzene to form ethylbenzene, the preferred alkylating agent is ethylene. In the alkylation of benzene to produce cumene, the preferred alkylating agent is propylene.

In the alkylation process of the present invention, the preferred mordenite zeolite catalyst has a silica/alumina molar ratio of at least 160:1. The overall yield of monoalkylated products approaches 100 percent when the monoalkylated benzene or monoalkylated substituted benzene obtained during the alkylation process, such as the alkylation of benzene to form either cumene (diisopropylbenzene being the major by-product) or ethylbenzene (diethylbenzene being the major by-product), are separated from the polyalkylated benzene or polyalkylated substituted benzene fraction by techniques known in the art, such as distillation, and then transalkylating the polyalkylated benzene or polyalkylated substituted benzene fraction in the presence of a mordenite zeolite catalyst having a silica/alumina molar ratio of at least 50:1 to form additional monoalkylated benzene or monoalkylated substituted benzene. A unique feature of the overall two bed monoalkylation process in the present invention is that the use of catalysts having a silica/alumina molar ratio of above about 160:1 in the alkylation process is superior to catalysts having lower silica/alumina molar ratios in that the selectivity and conversion to monoalkylated products is enhanced and the catalyst lifetime is longer than that of lower molar ratio catalysts under the reaction conditions described herein.

The catalyst useful in the practice of this invention is an acidic mordenite zeolite having a silica/alumina molar ratio of at least 30:1 for alkylation or a silica/alumina molar ratio of at least 50:1 for transalkylation. The catalyst has a Symmetry Index (SI) as defined hereinafter of at least about 1.0, and a porosity such that the total pore volume is in the range from about 0.18 cc/g to about 0.45 cc/g, and the ratio of the combined meso- and macropore volume to the total pore volume is in the range from about 0.25 to about 0.75. For the purposes of this invention, a micropore has a radius in the range of about 3 angstrom units (Å) to 10 Å, a mesopore has a radius in the range of 10 Å to 100 Å, and a macropore has a radius in the range of 100 Å to 1000 Å.

The catalyst of the invention is an acid-modified zeolite with interconnecting twelve-ring and eight-ring channels. Zeolites have framework structures that are formally constructed from silicate and aluminate tetrahedra that share vertices. The tetrahedra may be linked to form pores or channels. The size of the pores is determined by the number of tetrahedra in the ring. Twelve-ring zeolites contain rings formed from twelve tetrahedra. Eight-ring zeolites contain rings formed from eight tetrahedra. The zeolites of this invention contain interconnecting twelve-ring and eight-ring channels Examples of the zeolites suitable for use in this invention are mordenite, offretite and gmelinite. Mordenite-like zeolites, such as ECR-1 which is described in U.S. Pat. No. 4,657,748, and intergrowths of mordenite with other zeolites are also suitable catalysts: as are zeolites having a one-dimensional pore system with twelve-ring channels, such as type L or related zeolites. Preferably the catalyst is an acidic mordenite zeolite.

The alkylation catalyst useful in this invention is prepared by a process which comprises dealumination of mordenite zeolite having a silica/alumina molar ratio less than 30:1 and a crystalline structure which is determined by X-ray diffraction to possess a Symmetry Index (SI) of from about 0.5 to about 1.3 and more preferably of from about 0.7 to about 1.3 under conditions sufficient to remove an amount of alumina sufficient to provide a catalyst having the desired silica/alumina molar ratio.

Natural mordenite is an aluminosilicate whose typical unit cell contents are assigned the formula $Na_8 [(AlO_2)_8 (SiO_2)_{40}.24 H_2O]$. Mordenite is the most siliceous natural zeolite with a silicon/aluminum mole ratio (Si/Al) of about 5:1. The dimensions of the twelve-ring pores are about $6.7 \times 7.0$ Å; the dimensions of the eight-ring pores are about $2.9 \times 5.7$ Å. The structure and properties of mordenite zeolite are described in Zeolite Molecular Sieves, by Donald W. Breck (John Wiley & Sons, 1974), at pages 122–124 and $162 \times 163$, which is incorporated herein by reference.

The catalyst of this invention is prepared from a mordenite zeolite typically containing cations of the alkali or alkaline earth metals, or alternatively ammonium ions. Depending upon the source of the raw materials employed in preparing the starting mordenite, the latter may contain varying amounts of metal ions other then the above-identified ones. Mordenites prepared from clays, for example, may contain significant amounts of iron, lesser amounts of cobalt, copper and nickel, and even lesser amounts of other transition elements and rare earths. Mordenites prepared from fumed silica, however, may contain only trace amounts of these extraneous metals, since fumed silica is generally quite pure. The metal ions of the above-mentioned metals, such as sodium, magnesium, or calcium, which are often present in starting mordenite samples, may be present in trace amounts in the acidic mordenite catalyst of this invention. Preferably, the catalyst of the invention is prepared from a sodium mordenite zeolite; even more preferably, from a sodium mordenite zeolite having a Symmetry Index of from about 0.7 to about 1.3. The Symmetry Index is a dimensionless number obtained from the X-ray diffraction pattern of the sodium mordenite being measured in the hydrated form. Standard techniques are employed to obtain the X-ray data. The radiation is the $K\alpha_1$ line of copper, and a Philips Electronics spectrometer is used. The mordenite zeolites exhibit an X-ray diffraction pattern whose diffraction peaks have d-spacings corresponding to those of crystalline mordenites as reported by J. D. Sherman and J. M. Bennett in "Framework Structures Related to the Zeolite Mordenite," Molecular Sieves: J. W. Meier and J. B. Uytterhoeven, eds., Advances in Chemistry Series, 121, 1973, pp. 52–65. The Symmetry Index is defined as the sum of the peak heights of the [111] (13.45, $2\theta$) and 241] (23.17 $2\theta$) reflections divided by the peak height of the [350] (26.25 $2\theta$) reflection.

Four ordered crystalline structures have been proposed to describe the X-ray diffraction data available for natural and synthetic mordenite zeolites. (J. D. Sherman and J. M. Bennett, op. cit., p. 53.) The symmetries of these four structures are Cmcm, Cmmm, Imcm, and Immm as these terms are defined by N. F. M. Henry and K. Lonsdale in International Tables for X-ray Crystallography, 3rd Ed., Volume 1, Kynoch Press (1969). X-ray diffraction data indicate that mordenites are either physical admixtures or intergrowths of the Cmmm, Imcm, or Immm structures with the Cmcm structure. Thus, mordenites can be generally described as having a crystalline structure comprising a matrix of Cmcm symmetry having dispersed therein domains of Cmmm, Imcm, or Immm symmetry, or mixtures thereof. Preferably, the mordenite of this invention has a crystalline structure comprising a matrix of Cmcm symmetry having dispersed therein domains of Cmmm symmetry. The Symmetry Index is related to the symmetries of the crystals present in the mordenite sample. A Symmetry Index in the range from about 0.7 to about 1.3 provides the optimum sodium mordenite as starting material for the process of this invention.

The crystallite size of the original sodium mordenite may be any size which yields a catalyst selective for alkylating or transalkylating benzene or substituted benzene. Typically, the crystallite size may be in the range from about 500 Å to about 5000 Å. Preferably, the crystallite size is in the range from about 500 Å to about 2000 Å; more preferably, from about 800 Å to about 1500 Å. Generally, the crystallites form aggregates which may be used as such or bound into larger particles for the preparation of the catalyst to be used in the process of this invention. For example, extrudate can be made for a packed-bed reactor by compressing the aggregates into binderless particles of suitable sizes. Alternatively, the extrudate can be made via use of inert binders well-known to those in the art. Silica is the preferred binder. Typically, the concentration of binder ranges from about 0 to about 90 weight percent of the bound catalyst composition, preferably, from about 5 to about 70 weight percent of the bound catalyst composition, more preferably, from about 5 to about 40 weight percent of the bound catalyst composition.

The original sodium mordenite zeolite described hereinabove, or its equivalent, is treated to obtain the catalyst of the invention for use in the alkylation process. Intergrowths of mordenite zeolite with other zeolites are also suitable starting materials. The treatment involves contacting the mordenite with acid. In one preferred embodiment, the treatment involves contacting the mordenite with acid, calcining the acid-treated mordenite, and further contacting the calcined mordenite with strong acid. In an alternative preferred embodiment, the catalyst is prepared without being calcined.

The initial acid treatment serves to remove most of the sodium ions, or their equivalents, from the original mordenite. The treatment may remove a portion of the aluminum ions as well. Inorganic acids and organic acids are suitable compounds from which the hydrogen ions are obtained for the acid treatment. Examples of such acids are hydrochloric acid, hydrobromic acid, sulfuric acid, phosphoric acid, nitric acid, acetic acid, oxalic acid, and the like. Inorganic acids are the preferred source of hydrogen ions; with hydrochloric, nitric and phosphoric acids being more preferred and hydrochloric acid being most preferred. An equally acceptable initial treatment involves ion exchange with ammonium salts, such as ammonium chloride. By this method the sodium ions, or their equivalents, are removed, but the aluminum ions are not displaced. On heating the ammonium exchanged mordenite, ammonia is given off and the mordenite is converted to the acid form.

Typically, in the initial acid treatment the original sodium mordenite is slurried with an aqueous solution of the acid. The acid solution may have any concentration, providing the catalyst obtained possesses the properties and activity of the catalyst of this invention, these being described hereinafter. Preferably, the concentration of the aqueous acid solution is in the range from about 0.01N to about 6N: more preferably in the range from about 0.5N to about 3.0N. The relative quantities of aqueous acid solution to mordenite solid which are employed may vary. Typically, the ratio is less than about 15 cc acid solution per gram mordenite solid. Preferably, the ratio is in the range from about 5 cc acid solution per gram mordenite solid to about 10 cc acid solution per gram mordenite solid. The temperature and the duration of the contact of the mordenite with the acid solution may also vary. Preferably, the mordenite is contacted with the acid at a temperature in the range from about 10° C. to about 100° C. Generally, the contact time between the acid solution and the mordenite may vary from about 5 minutes to about several hours It is important that there be sufficient time for the acid solution to contact all of the mordenite particles. Preferably, the contact time is from about 5 minutes to about 60 minutes. The acid extraction, as described herein, may be repeated if desired. Afterwards, the mordenite is washed in water one or more times in order to rinse away soluble species from the mordenite. Preferably, the water wash is carried out at ambient temperature. Optionally, subsequent to the water wash the mordenite is dried in air at a temperature in the range from about 20° C. to about 150° C.

In one treatment, following the exchange with acid and drying in air, the acidic mordenite zeolite is calcined in air or heated in an inert atmosphere, such as nitrogen. It is believed that this heat treatment dislocates a portion of the aluminum from the zeolite framework: however, such a theory should not be taken as limiting of the scope of the invention. Preferably, the temperature of the calcination or heating is in the range from about 300° C. to about 800° C. More preferably, the temperature is in the range from about 500° C. to about 750° C. Most preferably, the temperature is from about 650° C. to about 750° C.

After calcining the acid-treated mordenite described hereinabove, the mordenite is subjected to an additional acid treatment for the purpose of further dealumination. The second acid treatment comprises contacting the calcined mordenite with a strong acid under conditions sufficient to produce the acidic mordenite catalyst of this invention. For the purposes of this invention a "strong" acid is defined as an acid which reacts essentially completely with the solvent to give the conjugate acid of the solvent. For example, if gaseous hydrogen chloride is dissolved in water, the acid-base reaction is complete to give the conjugate acid $H_3O+$ and $Cl-$. Preferably, the strong acid is an inorganic acid. More preferably, the strong acid is nitric acid, hydrochloric acid, or sulfuric acid. Most preferably, the strong acid is nitric acid. The concentration of the strong acid will vary depending on the acid selected. In general, the acid is employed in an aqueous solution of any concentration which provides for the extraction of aluminum from the calcined acidic mordenite, as described hereinafter. With nitric acid, for example, the concentration of the acid in the aqueous solution is preferably in the range from about 2N to about 15N. More preferably, the concentration of the acid is in the range from about 4N to about 12N. Most preferably, the concentration of the acid is in the range from about 6N to about 8N. The aqueous acid solution and the calcined mordenite are contacted in any ratio that provides the catalyst of the invention. Preferably, the ratio of aqueous acid solution to mordenite is in the range from about 3 cc acid solution per gram mordenite to about 10 cc acid solution per gram mordenite. More preferably, the ratio is about 5 cc acid solution per gram mordenite. The temperature and the duration of the contact may vary depending on the acid selected. Preferably, the mordenite is contacted with the acid solution at a temperature in the range from about ambient temperature taken as 22° C. to about 220° C. More preferably, the mordenite and the acid are contacted at a temperature which allows for boiling of the aqueous acid under atmospheric conditions. Preferably, the duration of the contact is from about 1 hour to about 6 hours: more preferably, from about 1 hour to about 3 hours; most preferably, for about 2 hours. When the contacting with strong acid is complete, the mordenite is filtered and washed repeatedly with water until the washings are acid-free. Preferably, the washed mordenite is heat treated and contacted with strong acid more than once. Lastly, the washed acidic mordenite zeolite is dried for several hours at a temperature in the range from about 100° C. to about 150° C. to remove physically adsorbed water. The dried acidic mordenite is activated by heating for about 2 hours at a temperature in the range from about 300° C. to about 700° C. This activation may drive off more strongly bound water and any residual adsorbates.

In an alternative embodiment, the original sodium mordenite is treated with acid and retreated with strong acid without the intermediate calcination step.

After the original sodium mordenite is treated with acid, optionally calcined, and retreated with strong acid according to the process of this invention, an acidic mordenite catalyst is obtained which is capable of converting benzene in a high conversion to either cumene or ethylbenzene having low levels of polyalkylated products, low levels of impurities, and a low bromine index. This catalyst exhibits special characteristics by which it may be identified, specifically, silica/alumina molar ratio and the Symmetry Index and porosity as defined hereinafter.

An additional characteristic of the catalyst is its minimal deactivation in the alkylation of benzene or substituted benzenes In the process of the present invention, the catalyst remains active for long periods of use. By remaining active, it is meant that the catalyst retains at least about 60, more preferably about 75 and most preferably about 90 percent of its activity for a period of at least about 500 hours of use, more preferably for at least about 750 hours of use and most preferably for at least about 900 hours of use. The catalyst preferably remains active significantly longer than 900 hours of use.

In the alkylation of the present invention, the catalyst, should it show any deactivation, may be regenerated by burning off the carbonaceous deposits. This may be effected by passing an oxygen containing gas over the catalyst at a temperature of 400°–700° C.

As a result of the acid extractions, the silica/alumina molar ratio ($SiO_2/Al_2O_3$) of the acidic mordenite catalyst is increased over that of the original sodium mordenite. Specifically, the acid-treated mordenite catalyst has a silica/alumina molar ratio of greater than 30:1. The selection of a catalyst having a specific silica/alumina ratio is significantly effected by process conditions and reactor configuration. Thus, it has now found that in a continuous flow alkylation process, the acid-treated mordenite catalyst preferably has a silica/alumina molar ratio of at least 160:1, more preferably at least 175:1, even more preferably at least 190:1. Generally the silica/alumina molar ratio of the acid-treated mordenite catalyst for the continuous flow alkylation process is not higher than about 2500:1, more preferably not higher than about 1000:1.

As a further result of the acid extractions and, optionally, calcination, the Symmetry Index of the mordenite catalyst is increased over that of the original mordenite. The Symmetry Index is as defined hereinbefore. Since the Symmetry Index is derived from X-ray data, the Index is related to the proportion of Cmcm, and Cmmm, Imcm, or Immm symmetries present in the catalyst. The increase in the Symmetry Index is indicative of the enrichment of the catalyst in the Cmcm component. For alkylations, a Symmetry Index of at least about 1 results in catalysts showing minimal deactivation that are capable of achieving high yields of monoalkylated benzenes. Preferably, the Symmetry Index ranges from about 1 to about 2.

A third property of the acidic mordenite catalyst, by which it is identified, is the porosity. All zeolites possess pores which form as a natural consequence of zeolite crystal growth. New pores or modifications of existing pores can occur on treating the zeolites, for example, with heat or acid as in the process of this invention. Typically, pores are classified into micropores, mesopores and macropores. For the purposes of this invention a micropore is defined as having a radius in the range from about 3 Angstrom units (3 Å) to 10 Å. Likewise, a mesopore is defined as having a radius in the range from 10 Å to 100 Å, while a macropore is defined as having a radius from 100 Å to 1000 Å. After calcination and strong acid treatment, the acidic mordenite catalyst of this invention possesses micro-, meso- and macropores. The porosity of the catalyst may be distinguished by the total pore volume defined as the sum of the volumes of the micro-, meso-, and macropores per gram catalyst. A catalyst of this invention has a total pore volume sufficient to provide a high yield of the desired monoalkylated benzene with low levels of polyalkylated products and low levels of impurities. Preferably, the total pore volume is in the range from about 0.18 cc/g to about 0.45 cc/g. The porosity may be further distinguished by the relative distribution of meso- and macropores, as found in the ratio of the combined meso- and macropore volume to the total pore volume. A catalyst of this invention has a ratio of combined meso- and macropore volume to total pore volume sufficient to provide a high yield of the desired monoalkylated aromatics with low levels of impurities. Preferably, the ratio of the combined meso- and macropore volume to total pore volume is in the range from about 0.25 to about 0.75.

The measurement of the porosity, described hereinabove, is derived from surface area and pore volume measurements of mordenite powders obtained on any suitable instrument, such as a Quantachrome Digisorb-6 unit, using nitrogen as the adsorbate at the boiling point of nitrogen, 77 K. The total pore volume (VT) is derived from the amount of nitrogen adsorbed at a relative pressure close to unity. It is accepted that this volume constitutes pores of less than 1000 Å in radius. As stated earlier, for the purposes of this invention pores with radius of 10 Å or less are called micropores. Pores with radius from 10 Å to 100 Å are called mesopores, and pores with radius from 100 Å to 1000 Å are called macropores. Pores with radius in the 10 Å to 1000 Å range are known in the literature as "transitional pores." The micropore volume ($V_m$) in the presence of "transitional pores" is obtained by the t-method. The difference between the total pore volume and the micropore volume is the transitional pore volume, ($V_t = V_T - V_m$). The cumulative pore distribution in the transitional pore range is used to calculate the relative volume contributions of mesopores and macropores. For example, the mesopore volume is calculated by multiplying the transitional pore volume by the fraction of the cumulative pore volume from 10 Å to 100 Å, ($V_{me} = V_t f_{me}$). The macropore volume is then simply obtained by subtracting the mesopore volume from the transitional volume, ($V_{ma} = V_t - V_{me}$). This approach ensures that the equation $V_T = V_m + V_{me} + V_{ma}$ is satisfied. The adsorption isotherms obtained for the mordenite catalysts of this invention are of Type I, which are described by the Langmuir equation. The Langmuir surface area is obtained from such equation. The methods used to obtain surface areas and pore volumes are described by S. Lowell in Introduction to Powder Surface Area (John Wiley and Sons, 1979), or in the manuals provided with the Digisorb-6 instrument made by the Quantachrome Corporation.

The acidic mordenite catalyst, identified hereinabove, is capable of adsorbing biphenyl into the intracrystalline pore system, and conversely desorbing biphenyl. Biphenyl adsorption is effected by exposing the acidic mordenite to biphenyl vapors at 100° C. for a time sufficient to obtain near constant weight. Preferably, the adsorption capacity of the acidic mordenite for biphenyl is about 5 weight percent. More preferably, the capacity is about 10 weight percent. Biphenyl desorption is effected by heating the mordenite-biphenyl sample in a dynamic helium atmosphere from 25° C. to about 1000° C. at a heating rate of about 10° C./minute. The desorption of biphenyl may be followed experimentally by thermal gravimetric analysis combined with gas phase chromatography and mass spectrometry (TGA-GC-MS). It is found that weakly adsorbed biphenyl produces a weight loss at temperatures below about 300° C.; whereas, strongly adsorbed biphenyl produces a weight loss at temperatures from about 300° C. to as high as 1000° C. The amount of strongly adsorbed biphenyl is estimated by subtracting the amount of weakly adsorbed biphenyl from the total amount of biphenyl desorbed from the sample. A fully treated mordenite catalyst of this invention exhibits a sharp weight loss at temperatures below about 300° C., and little or no weight loss from 300° C. to 1000° C. In contrast, acid-exchanged mordenite exhibits a sharp weight loss at temperatures below about 300° C., and a second weight loss starting at about 300° C. and extending to 1000° C. It is believed that the weakly adsorbed biphenyl is located in sites from which there is relatively easy exit: whereas the strongly adsorbed biphenyl is located in sites from which there is relatively difficult exit. Thus, the acidic mordenite catalyst of this invention provides easy access and egress to adsorbed biphenyl. Such a theory, however, should not be construed to be binding or limiting of the scope of the invention.

The catalyst useful in the process of this invention is not sensitive to the small amounts of water which may usually be present in benzene or substituted benzene. Accordingly, the benzene or substituted benzene reactant does not have to undergo a drying treatment, which is another advantage of the present process.

The ratio of the benzene or substituted benzene to catalyst may be any weight ratio which produces the desired monoalkylated benzene with a relatively high selectivity, the dialkylated benzene being the major by-product with low levels of tri-, tetra-, or higher polyalkylated products and a low level of other impurities. Preferred ratios will also be dependent on the way the process is operated. For example, in batch reactors, the weight ratio of benzene or substituted benzene to catalyst is preferably in the range from about 0.1:1 to about 2000:1. More preferably, the weight ratio is in the range from about 10:1 to about 500:1. Most preferably, the ratio is in the range from about 50:1 to about 100:1. Below the preferred lower limit of 0.1:1, the productivity will be very low. Above the preferred upper limit of 2000:1, the conversion of the aromatic compound may be low. In a continuous mode of operation the weight hourly space velocity (WHSV) of the overall feed with respect to catalyst is preferably in the range from about 0.5 to about 100. More preferably, the WHSV is in the range from about 0.5 to 20.

In an alkylation of benzene or substituted benzene, the molar ratio of benzene or substituted benzene to alkylating agent may vary depending on the identity of the alkylating agent, type of reaction such as batch or continuous, and reaction conditions such as temperature, pressure and weight hourly space velocity (WHSV). In a continuous alkylation process, the ratio of benzene or substituted benzene to alkylating agent is preferably at least 1:1, more preferably between about 1:1 and 10:1, and even more preferably between from about 1:1 to 3:1. When a continuous alkylation process is combined with a transalkylation process it is preferable that in the continuous alkylation process, the ratio of benzene or substituted benzene to alkylating agent is preferably between 1:1 and 3:1. More preferably, the ratio of benzene to alkylating agent is between about 1.7 and about 2.9, most preferably between about 2.0 and about 2.7. The preferred ratio may be lower in a batch reactor with the alkylating agent, such as propylene or ethylene, being supplied on demand.

In the alkylation of benzene or substituted benzene, the amounts of benzene or substituted benzene and of alkylating agent may be introduced to the reactor or reaction zone all at once or on demand in the case of a batch reaction. In the case of a continuous process, the benzene or substituted benzene and alkylating agent may be introduced to the reactor or reaction zone as separate feeds or as combined feeds. Further, either the benzene or substituted benzene and the alkylating agent may be introduced to the reactor or reaction zone as a single feed stream or split into a plurality of feed streams which are introduced into the reactor at different locations. In the latter case, at least one of the subsequent streams is introduced into the main feed stream after the reactants therein have at least partially reacted. For example, in a reactor containing one or more fixed catalyst beds, a subsequent stream is introduced after the main stream has passed at least one catalyst bed or a portion thereof, and before the main stream enters a further catalyst bed or a portion thereof. In the continuous process of the present invention, preferably, a plurality of catalyst containing reaction zones in fluid connection in series is used, wherein the whole of the benzene or substituted benzene is delivered to a first reaction zone, and a series of fractions of alkylating agent are delivered respectively to the first reaction zone and between each pair of contiguous reaction zones. The reaction zones may be operated with the same or different alkylation catalyst and at the same or different temperature and WHSV. More preferably, two to twenty catalyst containing reaction zones are used and a corresponding number of alkylating agent streams. Operating the process in this way has been found to increase the selectivity towards the monoalkylated product, compared to supplying the whole of the alkylating agent to the first reaction zone. Furthermore, by feeding the alkylating agent as a series of fractions, a better control of the reaction temperature is possible for this exothermic reaction. Alternatively or additionally, the reaction zones may be cooled by conventional means.

The contacting of the benzene or substituted benzene with the alkylating agent in the presence of the catalyst may occur in a reactor of any configuration. Batch-type and continuous reactors, such as fixed bed, slurry bed, fluidized bed, catalytic distillation, or countercurrent reactors, are suitable configurations for the contact. Preferably, the reactor is a continuous reactor.

The continuous process of the invention is carried out under conditions sufficient to keep the reaction mixture in the liquid phase. This means that substantially no gaseous zone is present in the reactor. With substantially no gaseous zone is meant, that the gaseous zone comprises at the most 5 percent by volume of the reaction zone, preferably at the most 1 percent by volume. Most preferably, the reactor is operated in a full liquid mode. The presence of a substantial gaseous zone would lead to an accumulation of the alkylating agent therein, which under the prevailing conditions would polymerize. This in its turn would lead to a decrease in selectivity and to an increase in deactivation of the catalyst. The benzene or substituted benzene may be in the molten, liquid form or in solution. The alkylating agent may be introduced in the liquid or gaseous state, and should substantially dissolve in the liquid phase. The catalyst may be used in various forms, such as a fixed bed, moving bed, or fluidized bed.

In the continuous alkylation process, the contacting of the reactants in the presence of the catalyst may occur at any temperature and pressure conditions sufficient to keep the reaction mixture in the liquid phase. Typically, the temperature is in the range from about 100° C. to about 300° C. These temperatures are relatively mild for zeolite catalyzed type alkylation processes. Below the lower limit of 100° C. the reaction proceeds slowly. In one preferred mode of the present process benzene is contacted with propylene as alkylating agent and the temperature is in the range from about 120° C. to about 250° C. In another preferred mode benzene is contacted with ethylene as alkylating agent and the temperature is in the range from about 170° C. to about 280° C. These conditions are rather mild for the production of cumene and ethylbenzene, respectively, in a zeolite catalyzed alkylation process. Following the alkylation of the benzene or substituted benzene, the product mixture may be separated by standard techniques. The desired monoalkylated products, such as for example cumene or ethylbenzene, are separated from the starting materials and by-products by techniques known in the art such as distillation. Normally, when using a distillation sequence as the separation technique, the benzene or substituted benzene starting material may be obtained as a first fraction, which may partially be recycled to the alkylation step and/or partially be fed to an optional subsequent transalkylation step. As a second fraction in the distillation sequence substantially pure monoalkylated product may be recovered. A third fraction may be separated which contains polyalkylated benzene or polyalkylated substituted benzene products and heavies and by-products like for example diphenyl alkanes. Alternatively and preferably a third fraction is collected containing primarily dialkylated products and optionally tri- and/or tetra-alkylated products. This latter third fraction, preferably containing no tetra-alkylated products, may be fed to a subsequent transalkylation process.

According to a further aspect of the invention, a polyalkylated benzene or polyalkylated substituted benzene fraction separated from the reaction product of the alkylation process as described hereinbefore is subjected to transalkylation by contacting the polyalkylated benzene or polyalkylated substituted benzene fraction with benzene or substituted benzene in the presence of a suitable transalkylation catalyst to produce monoalkylated benzene or monoalkylated substituted benzene.

The polyalkylated benzene or polyalkylated substituted benzene fraction obtained in the alkylation process of the present invention comprises a major portion of the dialkylated product and minor portions of the tri- and optionally but less preferably tetra- and higher polyalkylated products. As dialkylated products generally act as transalkylating agent under milder conditions than the higher-alkylated products this fraction is a very suitable transalkylating agent for the benzene or substituted benzene in the transalkylation step.

In the transalkylation, the polyalkylated benzene or polyalkylated substituted benzene fraction preferably is contacted with benzene or substituted benzene in the presence of a catalyst comprising an acidic mordenite zeolite having a silica/alumina molar ratio of at least 50:1. This transalkylation catalyst may be any prior art acidic mordenite zeolite having a silica/alumina molar ratio of at least 50:1 and having transalkylation activity.

It is preferred, however, that the catalyst used in the transalkylation additionally has a crystalline structure which is determined by X-ray diffraction to have a Symmetry Index of at least 1. The overall selectivity of monoalkylated product achieved in the alkylation-transalkylation process of the present invention, based on the benzene or substituted benzene used, is very high, preferably at least 97 mole percent and more preferably at least 99 mole percent. Thus an overall process is obtained having a relatively low amount of recycled benzene or substituted benzene, combined with substantially 100 percent conversion of the alkylating agent and a very high selectivity of monoalkylated product. Preferably, the catalyst used in the transalkylation has a Symmetry Index of between 1 and about 2. This transalkylation catalyst shows little or no deactivation and is capable of converting compounds like diphenyl alkanes, such as diphenyl ethane, which are produced in the alkylation process as undesired by-products, to the desired monoalkylated products, optionally in a separate diphenyl alkane conversion step. It is surprising that diphenyl alkane is also converted to monoalkylated product and benzene as this is not transalkylation in the usual meaning. Different from a transalkylation reaction, this conversion requires an additional hydrogen atom.

It is preferred that the catalyst used in the transalkylation has a silica/alumina molar ratio of between 50:1 and about 500:1. The transalkylation catalyst may comprise an inert binder. Binders known to be useful with mordenite zeolite catalysts, such as for example silica, are useful for this purpose. The binder may comprise between about 0 and 90 weight percent of the bound catalyst composition. Preferably, the binder comprises between about 5 and 70 weight percent, more preferably between about 5 and 40 weight percent. In a most preferred embodiment, the binder is silica.

In a continuous mode of operation the WHSV the transalkylation feed with respect to the transalkylation catalyst is preferably in the range from about 0.1 to about 100. More preferably, the WHSV is in the range from about 0.1 to 20.

In the transalkylation process, the molar ratio of the total benzene groups present in the benzene or substituted benzene and in the polyalkylated benzene or polyalkylated substituted benzene fraction, to the total of alkylated groups on the polyalkylated benzene or polyalkylated substituted benzene is preferably at least : 1.5:1. In case of a lower ratio the selectivity to the monoalkylated product is decreased. More preferably, the molar ratio is from about 2:1 to about 4:1.

The benzene or substituted benzene and transalkylating agent may be introduced to the reactor or reaction zone all at once or on demand or by multiple injection as in the case of a batch reaction, or in the case of a continuous transalkylation process as separate feeds or as combined feeds. Further, in the case of a continuous transalkylation process, either the benzene or substituted benzene and the transalkylating agent may be introduced to the reactor or reaction zone as a single feed stream or split into a plurality of feed streams which are introduced into the reactor at different locations. In the transalkylation process of the present invention preferably a plurality of catalyst containing reaction zones in fluid connection in series is used, wherein the whole of the benzene or substituted benzene is delivered to a first reaction zone, and a series of fractions of transalkylating agent are delivered respectively to the first reaction zone and between each pair of contiguous reaction zones. Operating the process in this way increases the selectivity towards the monoalkylated product compared to supplying the whole of the transalkylating agent to the first transalkylation reaction zone.

The contacting of the benzene or substituted benzene with the transalkylating agent in the presence of the transalkylation catalyst may occur in a reactor of any configuration. Batch-type and continuous reactors, such as fixed bed, slurry bed, fluidized bed, catalytic distillation, or countercurrent reactors, are suitable configurations for the contact. Preferably, the reactor is a continuous flow reactor.

In a continuous transalkylation of the present invention, the reaction is preferably carried out under : conditions sufficient to keep the reaction mixture in the liquid phase. Most preferably, the reactor is operated in a substantially full liquid mode. The benzene or substituted benzene and the transalkylating agent may be in the molten, liquid form or in solution. The catalyst may be used in various forms, such as a fixed bed, moving bed, fluidized bed, in suspension in the liquid reaction mixture, or in a reactive distillation column.

In a continuous transalkylation process, the contacting of the reactants in the presence of the catalyst may occur at any temperature and pressure conditions sufficient to keep the reaction mixture in the liquid phase. Typically, in the transalkylation the temperature is in the range from about 140° C. to about 300° C. These temperatures are relatively mild for zeolite catalyzed type transalkylation processes. In one preferred mode of the present transalkylation step a polyisopropylated benzene fraction as the polyalkylated benzene fraction is contacted with benzene and the temperature is in the range from about 140° C. to about 250° C. In another preferred mode a polyethylated benzene fraction as the polyalkylated benzene fraction is contacted with benzene and the temperature is in the range from about 200° C. to about 300° C.

The pressure in the reactor may be any pressure sufficient to keep the reaction mixture as a liquid under reaction conditions. The required pressure will change depending on temperature and reactants employed. Preferably, the pressure in the reactor is in the range from about 10 bar to about 200 bar. More preferably, the pressure is in the range from about 20 bar to about 100 bar.

The transalkylation, when performed in the presence of the preferred transalkylation catalyst, does not require the addition of hydrogen to the transalkylation feed. Prior art transalkylation processes are frequently carried out in the presence of hydrogen in order to remove carbonaceous deposits from the catalyst in order to limit deactivation thereof. In view of the minimal deactivation of the preferred transalkylation catalyst in the present process, no addition of hydrogen is required. The catalyst, should it show any deactivation, may be regenerated by burning off the carbonaceous deposits. This may be effected by leading an oxygen-containing gas over the catalyst at a temperature of 400°–700° C.

For the purposes of this invention, the term "benzene conversion" refers to the mole percent of benzene or substituted benzene which reacts to form alkylated products.

Likewise, the term "benzene selectivity" refers to the mole percent of reacted benzene which is converted to desired products, such as cumene or ethylbenzene, or to polyalkylated products. Smaller amounts of various by-products such as the o-, p- and m-isomers of diisopropylbenzene and other alkylated benzenes such as n-propylbenzene, butylbenzenes and xylenes are also formed. Typically, the benzene selectivity to cumene or ethylbenzene ranges from about 70 mole percent to about 99 mole percent.

Another measure of selectivity is the "propylene selectivity" or "ethylene selectivity" which refers to the mole percent of propylene or ethylene which is converted to cumene or ethylbenzene respectively. Preferably, the propylene selectivity or ethylene selectivity is at least about 55 mole percent up to about 99 mole percent.

The concept of simultaneous high conversion and high selectivity to desired product may be expressed conveniently in terms of yield. For the purposes of the present invention, the term "yield" refers to the numerical product of conversion and selectivity. For example, a process to produce cumene according to the present invention operating at a benzene conversion of 15 percent, and a selectivity to cumene of 85 percent, would have a yield of cumene of 12.75 percent, which is the numerical product of 15 percent and 85 percent. Typically, the yield of cumene or ethylbenzene achieved in the process of this invention, not considering any recycle or reactants, is at least about 10 mole percent and is preferably at least about 15 mole percent.

An additional factor that is important is the presence of various impurities in the product. Even very small amounts of certain impurities such as n-propylbenzene or propylene oligomers in the case of cumene, or xylenes in the case of ethylbenzene, create significant problems in various applications. Processes run under different conditions result in different levels of impurities. Thus, a particular advantage of the overall alkylation-transalkylation process of the present invention is the low impurity levels. In the case of cumene production, low levels of oligomers as indicated by low bromine index is also important. In cumene production, the bromine index is preferably no greater than about 100, more preferably no greater than about 50 and most preferably no greater than about 20. Cumene produced by the process of this invention preferably contains less than about 1000 parts per million (ppm) impurities, more preferably less than about 200 ppm. Ethylbenzene produced by the process of this invention preferably has less than about 200 ppm xylene impurities, more preferably less than about 100 ppm.

SPECIFIC EMBODIMENTS

The following examples are given to illustrate the catalyst and the process of this invention and should not be construed as limiting its scope. All percentages in the examples are mole percent unless otherwise indicated.

EXAMPLE 1

Catalyst Preparation

Catalyst C-1, not an embodiment of the invention, is an H-mordenite with a Symmetry Index of 0.88 with a $SiO_2/Al_2O_3$ ratio of 15.2 and 20 weight percent of a silica binder is used without further treatment. This is typical of commercially available mordenite. Its characteristics are given in Table I below.

Catalyst E-1, with a Symmetry Index of 2.1, is selected from commercially available hydrogen mordenites and used without further treatment and has the characteristics listed in Table I below. It also comprises 20 weight percent silica binder.

Catalyst E-2 is prepared by slurrying 300 g of Na-mordenite with a $SiO_2/Al_2O_3$ ratio of 19 and a Symmetry Index of 1.26 with 3000 ml of a 1M HCl solution for 30 minutes at room temperature. The product is washed with three 2000 ml portions of water and dried at 150° C. overnight. The dry solid is stirred in 1500 ml of 6M $HNO_3$ and heated under reflux for two hours. The product is washed with two 2000 ml portions of water and dried at 150° C. in air overnight. The Symmetry Index is 1.68. The characteristics of the catalyst are also listed in Table I below.

Catalyst E-3 is prepared from Na-mordenite with a SiO$_2$/Al$_2$O$_3$ ratio of 15 and a Symmetry Index of 0.97 using the procedure described for E-3. The Symmetry Index is 1.38. The characteristics of the catalyst are also listed in Table I below.

Catalyst E-4 has a Symmetry Index of 1.85 and is selected from commercially available hydrogen mordenite and used without further treatment. It has the characteristics listed in Table I below. This catalyst also includes 20 weight percent of a silica binder.

TABLE I

| Catalyst | SiO$_2$/Al$_2$O$_3$ (Molar Ratio) | Si/Na (Atomic Ratio) | BET (m$^2$/g) | Micro Pore Volume (ml/g) | Meso-Pore Volume (ml/g) | Macro-pore Volume (ml/g) | Total Pore Volume (ml/g) |
|---|---|---|---|---|---|---|---|
| C-1 | 15.2 | 96 | 389 | 0.190 | 0.023 | 0.036 | 0.244 |
| E-1 | 38 | 466 | 489 | 0.180 | 0.080 | 0.034 | 0.294 |
| E-2 | 84 | 1490 | 378 | 0.159 | 0.038 | 0.032 | 0.229 |
| E-3 | 108 | 4200 | 418 | 0.173 | 0.083 | 0.062 | 0.318 |
| E-4 | 156 | 4868 | 389 | 0.160 | 0.139 | 0.324 | 0.624 |

Catalysts C-1 and E-4 are extrudates with a diameter of about 1.5 mm. Catalysts E-1, E-2 and E-3 are crushed filtered particles of about 4 to 5 mm. Catalysts E-1 through E-4 are determined by X-ray diffraction to have Cmcm symmetry having dispersed therein domains of Cmmm symmetry.

Transalkylation to Produce Cumene

Reactant feed is a mixture of distilled heavies from a cumene production and recycled benzene. The feed contains about 61 weight percent benzene; about 9 weight percent p-diisopropylbenzene (DIPB): about 8 weight percent m-DIPB: about 6 weight percent cumene; about 4 weight percent o-DIPB: about 3 weight percent 2-methyl, 2-phenylpentane: about 1 weight percent 3-methyl, 3-phenylpentane and about 8 weight percent various other impurities.

The pressure is 36 bar and the WHSV (feed weight hourly space velocity) is varied between about 0.4 and 0.8 hr$^{-1}$. Reactor effluent is cooled to room temperature prior to analysis which is performed on line by gas chromatography.

EXAMPLE 2

Transalkylation Using Catalyst E-3

In this experiment, the molar ratio of benzene to diisopropylbenzene is 5.9 and the WHSV is either 0.46 hr$^{-1}$ or 0.72 hr$^{-1}$ as shown in the tables below. The temperature is varied and conversion and selectivity are measured at 140° C., 150° C. and 155° C. These results are shown in Table II below.

TABLE II

| | (CATALYST E-3) | | | |
|---|---|---|---|---|
| | Temperature (°C.) | | | |
| | 150 | 150 | 140 | 175 |
| Conversion (%) | | | | |
| m-DIPB | 59 | 70 | 27 | 75 |
| o-DIPB | 27 | 40 | 16 | 88 |
| p-DIPB | 82 | 86 | 68 | 88 |
| Total | 62 | 70 | 42 | 83 |
| Selectivity (%) | | | | |
| DIPB | 92 | 91 | 92 | 87 |
| Benzene | 102 | 105 | 102 | 114 |
| WHSV (hr$^{-1}$) | 0.72 | 0.46 | 0.46 | 0.46 |

TABLE II-continued

| | (CATALYST E-3) | | | |
|---|---|---|---|---|
| | Temperature (°C.) | | | |
| | 150 | 150 | 140 | 175 |
| Time (hrs) | 90 | 60 | 170 | 100 |

The data in Table II demonstrates the long life of the catalyst used in the process of the present invention. No deactivation is observed when the reaction is run for the cumulative time indicated under the conditions shown.

The amount of specified by-products and of cumene in the feed and effluent are measured. These measurements are done at a WHSV of 0.46 hr$^{-1}$. The results are shown in Table III below.

TABLE III

| | (CATALYST E-3) | | | |
|---|---|---|---|---|
| | | Reactor Effluent at | | |
| | Reactor Feed | 140° C. | 150° C. | 175° C. |
| Ethylbenzene (ppm) | 170 | 50 | 80 | 646 |
| n-propylbenzene (ppm) | — | 90 | 300 | 4722 |
| t-butylbenzene (ppm) | 135 | 915 | 820 | 825 |
| Cumene (wt %) | 4 | 17 | 25 | 28 |

The data above indicates that impurity production increases significantly at higher temperatures.

Using the conditions described above, the transalkylation reaction using Catalyst E-3 is run for a total of about 900 hours. No deactivation is shown over this time period.

EXAMPLE 3

Transalkylation Using Catalyst E-2

In this experiment, the molar ratio of benzene to diisopropylbenzene is 5.9 and the WHSV is 0.72 hr$^{-1}$. The temperature is varied and conversion and selectivity are measured at 140° C., 150° C. and 160° C. These results are shown in Table IV below.

TABLE IV

| | (CATALYST E-2) | | |
|---|---|---|---|
| | Temperature (°C.) | | |
| | 140 | 150① | 160 |
| Conversion (%) | | | |
| m-DIPB | −5 | 33 | 63 |
| o-DIPB | 11 | 22 | 36 |
| p-DIPB | 54 | 70 | 84 |
| Total | 23 | 46 | 66 |
| Selectivity (%) | | | |
| DIPB | 95 | 95 | 93 |
| Benzene | 85 | 98 | 97 |

TABLE IV-continued

| (CATALYST E-2) | | | |
|---|---|---|---|
| | Temperature (°C.) | | |
| | 140 | 150① | 160 |
| Time (hrs) | 120 | — | 210 175 |

①Slight deactivation is observed at this temperature. The first column represents results at the beginning of the reaction at this temperature and the second column indicates results after 210 hours.

The data in Table IV demonstrates the long life of this catalyst used in the process of the present invention. Slight deactivation is shown at 150° C. In this situation, the conversion of DIPB drops from 46 to 42 percent. At 140° C. and 160° C., no deactivation is observed.

The amount of specified by-products and of cumene in the feed and effluent are measured. These measurements are done at a WHSV of 0.46 hr$^{-1}$. The results are shown in Table V below.

TABLE V

| (CATALYST E-2) | | | |
|---|---|---|---|
| | Reactor Feed | Reactor Effluent at | |
| | | 150° C. | 160° C. |
| Ethylbenzene (ppm) | 20 | 50 | 100 |
| n-propylbenzene (ppm) | <10 | 150 | 560 |
| t-butylbenzene (ppm) | 130 | 840 | 790 |
| s-butylbenzene (ppm) | 40 | 190 | 370 |
| Cumene (wt %) | 4.6 | 18.0 | 24.5 |

EXAMPLE 4

Transalkylation Using Catalysts E-1 and E-4

In this experiment, the molar ratio of benzene to diisopropylbenzene is 5.8 and the WHSV is either 0.45 hr$^{-1}$ or 0.74 Hr$^{-1}$. The temperature is varied and conversion and selectivity are measured at 150° C. and 175° C. These results are shown in Table VI below.

TABLE VI

| (CATALYSTS E-4 AND E-1) | | | | | |
|---|---|---|---|---|---|
| | Temperature (°C.) | | | | |
| | 150 | 150 | 150 | 150 | 175 |
| Catalyst | E-4 | E-4 | E-1 | E-1 | E-4 |
| Conversion (%) | | | | | |
| m-DIPB | <1 | 18 | 73 | 73 | 71 |
| o-DIPB | 5 | 14 | 43 | 69 | 66 |
| p-DIPB | 58 | 65 | 87 | 87 | 86 |
| Total | 25 | 37 | 73 | 78 | 76 |
| Selectivity (%) | | | | | |
| DIPB | 96 | 94 | 93 | 92 | 91 |
| Benzene | 95 | 99 | 110 | 120 | 110 |
| WHSV (hr$^{-1}$) | 0.74 | 0.45 | 0.75 | 0.45 | 0.74 |
| Time (hrs) | 70 | 110 | 70 | 70 | 110 |

The data in Table VI demonstrates the long life of the catalysts used in the process of the present invention.

The amount of specified by-products and of cumene in the feed and effluent are measured. These measurements are done at a WHSV of 0.46 hr$^{-1}$. The results are shown in Table VII below.

TABLE VII

| (CATALYSTS E-4 AND E-1) | | | | | |
|---|---|---|---|---|---|
| | Reactor Feed | Reactor Effluent at | | | |
| | | 150° C. | 150° C. | 175° C. | 150° C. | 150° C. |
| Catalyst | | E-4 | E-4 | E-4 | E-1 | E-1 |
| Ethylbenzene (ppm) | <10 | <10 | 90 | 150 | 140 | 230 |
| n-propylbenzene (ppm) | <10 | 10 | 120 | 510 | 700 | 1210 |
| t-butylbenzene (ppm) | 200 | 1020 | 990 | 870 | 640 | 620 |
| s-butylbenzene (ppm) | <10 | 100 | 140 | 500 | 410 | 560 |
| WHSV (hr$^{-1}$) | — | 0.74 | 0.45 | 0.74 | 0.75 | 0.45 |
| Cumene (wt %) | 5.8 | 13.8 | 17.5 | 28.7 | 28.0 | 29.1 |

EXAMPLE 5

Bromine Index in Transalkylation Product

Using Catalysts E-1 and E-4 and the procedure described above for the transalkylation reaction, cumene is produced at the temperatures and WHSV shown in Table VIII. The bromine index of the cumene is measured using ASTM D-1492-7B. Results obtained are shown in Table VIII below.

TABLE VIII

| Catalyst | Temperature (°C.) | WHSV (hr$^{-1}$) | Bromine Index (mg/100 g) |
|---|---|---|---|
| E-1 | 130 | 0.78 | 3 |
| | 140 | 0.74 | 5 |
| | 150 | 0.75 | 2 |
| | 150 | 0.46 | 3 |
| | 160 | 0.73 | 3 |
| E-4 | 150 | 0.76 | 2 |
| | 150 | 0.46 | 5 |
| | 175 | 0.75 | 12 |

COMPARATIVE EXAMPLE 1

Transalkylation Using Catalyst C-1 (Not an Embodiment of the Invention)

Catalyst C-1 is tested using similar conditions and shows significant deactivation after 110 hours of use. The percentage conversion of DIPB drops from about 56 percent to about 15 percent in this time period. The levels of impurities produced at the highest activity are 320 ppm n-propylbenzene, 670 ppm t-butylbenzene and 290 ppm s-butylbenzene.

EXAMPLE 6

Alkylation of Benzene with Propylene Using Catalyst E-4

A feed stream of benzene, propylene and propane is subjected to alkylation at various temperatures. The content of the feed stream is varied. Feed Stream 1 is 91.4 weight percent benzene, 8.5 weight percent propylene and 0.1 weight percent propane (5.8 molar ratio of benzene to propylene). Feed Stream 2 is 91.0 weight percent benzene, 8.9 weight percent propylene and 0.1 weight percent propane (5.5 molar ratio of benzene to propylene). Feed Stream 3 is 87.4 weight percent benzene, 12.4 weight percent propylene and 0.2 weight percent propane (3.8 molar ratio of benzene to propylene). Feed Stream 4 is 93.4 weight percent benzene, 6.5 weight percent propylene and 0.1 weight percent propane (7.7 molar ratio of benzene to propylene). The results are presented in Table IX below.

TABLE IX
(CATALYST E-4)

| Temp. (°C.) | Benzene Selectivity (%) | Propylene Selectivity (%) | DIPB Selectivity (%) | m-DIPB Selectivity (%) | o-DIPB Selectivity (%) | p-DIPB Selectivity (%) | Time (Hr) | Reactant Feed Composition |
|---|---|---|---|---|---|---|---|---|
| 130 | 71.1 | 54.6 | 28.5 | 4.9 | — | 23.6 | 22 | 1 |
| 145 | 74.0 | 59.2 | 25.0 | 9.9 | — | 15.1 | 22 | 1 |
| 155 | 78.8 | 65.6 | 20.1 | 12.2 | — | 7.9 | 24 | 1 |
| 165 | 86.4 | 73.6 | 13.7 | 9.3 | — | 4.4 | 30 | 1 |
| 175 | 91.6 | 83.4 | 7.9 | 5.3 | — | 2.6 | 80 | 1 |
| 185 | 94.8 | 88.0 | 5.1 | 3.3 | — | 1.7 | 48 | 2 |
| 175 | 91.1 | 83.0 | 8.6 | 5.7 | — | 2.9 | 24 | 3 |
| 175 | 94.7 | 87.0 | 5.1 | 3.4 | — | 1.7 | 45 | 4 |

EXAMPLE 7

Bromine Index in Alkylation Product

Using Catalyst E-4 and the general process described in Example 6 above, the bromine index of the cumene produced at various temperatures and benzene/propylene ratios is measured using ASTM D-1492-7B. The results obtained are shown in Table X below.

TABLE X

| Temperature (°C.) | Benzene/Propylene Molar Ratio | Bromine Index (mg/100 g) |
|---|---|---|
| 145 | 5.8 | 2 |
| 155 | 5.8 | <4 |
| 165 | 5.8 | <1 |
| 175 | 5.8 | <1 |
| 185 | 5.5 | <1 |
| 175 | 3.8 | <1 |
| 175 | 7.7 | <1 |

EXAMPLE 8

Alkylation of Phenol

A 100-g portion of phenol, 50 g of 1-octene and 100 g of 1,3,5-triisopropylbenzene are reacted in the presence of a dealuminated mordenite catalyst having a silica/alumina ratio of about 156. The reactants are contacted at 200° C. for 2 hours at a starting pressure of 38 psig. The product formed is colorless p-octylphenol. As determined by gas chromatography, the conversion of phenol is 40 percent, the conversion of octene is 80 percent and the p-octylphenol formed is at least 98 percent pure.

EXAMPLE 9

Preparation of Ethylbenzene

Using the general procedure described in Example 6, benzene is alkylated with ethylene to form ethylbenzene. The catalyst used has a $SiO_2/Al_2O_3$ ratio of 44, the BET is 403 m$^2$/g, the micropore volume is 0.137 ml/g, the mesopore volume is 0.070 ml/g, the macropore volume is 0.040 ml/g, the total pore volume is 0.237 ml/g and the Symmetry Index is 1.52. The ratio of ethylene to benzene is 0.41. The temperature is 220° C. and the pressure is 36 bar. The yield of ethylbenzene is 32.9 percent. The concentration of impurities are: toluene, 250 ppm; xylenes, 60 ppm; cumene, 220 ppm; n-propylbenzene, 150 ppm; ethyltoluene, 140 ppm; and butylbenzene, 200 ppm. No deactivation was observed after 140 hours of operation.

EXAMPLE 10

Catalyst Preparation

Alkylation catalysts A-1 and A-2 are prepared from Na-mordenite having a $SiO_2/Al_2O_3$ ratio of 19 and a Symmetry Index of about 1.2 according to substantially the same procedure. The Na-mordenite is ion-exchanged to remove sodium, then calcined. The product is leached with HCl to give a H-mordenite having a $SiO_2/Al_2O_3$ ratio of about 220 (catalyst A-1) and 196 (catalyst A-2). The H-mordenite is next pelletized with 20 percent silica binder. Finally, the pellets are calcined at 750° C. The characteristics of catalyst A-1 are as follows: Symmetry Index of 1.85: BET of 389 m$^2$/g; total pore volume of 0.374 ml/g; micro pore volume of 0.156 ml/g; meso pore volume of -0.140 ml/g; macro pore volume of 0.078 ml/g and meso+macro pore volume/ total pore volume of 0.58. For catalyst A-2: Symmetry Index of 1.98; BET of 392 m$^2$/g; total pore volume of 0.384 ml/g; micro pore volume 0.158 ml/g; meso pore volume of 0.135 ml/g; macro pole volume of 0.91 ml/g; and meso+macro pore volume/total pore volume of 0.59.

Transalkylation catalyst T-1 is prepared in a procedure similar to that of Catalyst A-1 using a starting sodium mordenite having a silica/alumina ratio of about 15 and a Symmetry Index of about 1.0. It is exchanged with 1.0N HCl to remove sodium and subsequently washed and calcined at 500° C. for 2 hours. Then it is extracted under reflux conditions with 6N HCl for 2 hours, washed and dried at 110° C., to give a silica/alumina ratio of about 81. This dealuminated mordenite is then mixed with 20 weight percent silica binder and calcined at 700° C. to give a catalyst with a Symmetry Index of 1.42; a benzene adsorption capacity of 13.7 percent (w/w); a BET of 382 m$^2$/g; total pore volume of 0.341 ml/g; a macro pore volume of 0.156 ml/g; and a meso+macro pore volume/ total pore volume of 0.54.

Catalysts A-1, A-2, and T-1 are determined by X-ray diffraction to have Cmcm symmetry having dispersed therein domains of Cmmm symmetry.

In the following experiments a continuous flow fixed catalyst bed type reactor was used.

EXAMPLE 11

Alkylation of Benzene with Ethylene

A feed stream of benzene and ethylene having a benzene to ethylene mole ratio of 2.22 is subjected to alkylation over catalyst A-2 at 250° C. and a pressure of 36 bar. The WHSV of the feed stream is about 1. The reactor effluent contains 24.9 weight percent ethylbenzene, 58.0 weight percent benzene, 13.5 weight percent diethylbenzene (m-diethylbenzene, 8.48 percent; p-diethylbenzene 4.06; o-diethylbenzene, 0.94 percent), and 3.30 weight percent triethylbenzene. No xylenes are observed. The ethylene conversion is 100 percent. The benzene conversion is 31 percent. The catalyst has high stability after 250 continuous hours of operation.

EXAMPLE 12

Alkylation of Benzene with Ethylene

A feed stream of benzene and ethylene having an overall benzene to ethylene ratio of 2.27 is subjected to alkylation over catalyst A-1 at 220° C. and a pressure of 50 bar. The WHSV of the feed stream is about 1. The ethylene feed is split in two parts: 50 percent of the ethylene is fed to the reactor inlet and 50 percent is introduced at half of the catalyst bed. The conversion of ethylene is 100 percent. The conversion of benzene is 33 percent. The reactor effluent contains 27.3 weight percent ethylbenzene, 57.9 weight percent benzene, 12.6 weight percent ortho- + meta- + paradiethylbenzenes, 1.8 weight percent triethylbenzene and 0.05 weight percent tetraethylbenzenes. No xylenes are observed. The catalyst has a high stability. The catalyst shows essentially no deactivation after over 600 hours of continuous use.

EXAMPLE 13

Alkylation of Benzene with Ethylene

A feed stream of benzene and ethylene having an overall benzene to ethylene ratio of 2.63 is subjected to alkylation over catalyst A-1 at 24020 C. and a pressure of 50 bar. The WHSV of the feed stream is about 2. The ethylene feed is split in two parts: 50 percent of the ethylene is fed to the reactor inlet and 50 percent at half of the catalyst bed. Conversion of ethylene is 100 percent. The conversion of benzene is 31 percent. The reactor effluent contains 26.1 weight percent ethylbenzene, 61.6 weight percent benzene, 10.6 weight percent ortho- + meta- + para-diethylbenzene, 1.4 weight percent triethylbenzene and 0.04 weight percent tetraethylbenzene. No xylenes are observed. The catalyst shows essentially no deactivation after over 500 hours of continuous use.

EXAMPLE 14

Transalkylation of Benzene with Polyethylbenzenes

A feedstream of 65.2 weight percent benzene, 29.8 weight percent meta + ortho + para- diethylbenzene, 1.5 weight percent triethylbenzenes, and 2.5 weight percent ethyl benzene having an overall benzene groups to ethylene groups mole ratio of 2.2 is subjected to transalkylation over catalyst T-1 at 235° C. and a pressure of 36 bar. The WHSV of the feed stream is about 1. The catalyst has a very high stability and shows essentially no deactivation after 3000 hours of continuous use. The conversion of diethylbenzenes is 68 percent. The conversion of triethylbenzenes is 15 percent. The selectivity of polyethylbenzenes to ethylbenzene is 97 percent.

EXAMPLE 15

Transalkylation of Benzene with Polyethylbenzene

A feedstream of 69.6 weight percent benzene, 26.5 weight percent meta- + ortho- + para-ethylbenzene, 1.4 weight percent triethylbenzene, and 2.5 weight percent ethylbenzene having an overall benzene groups to ethylene groups mole ratio of 2.5 is subjected to transalkylation over catalyst T-1 at 260° C. and a pressure of 36 bar. The WHSV of the feedstream is 2.7. The effluent contains 32.2 weight percent ethylbenzene. Conversion of the diethylbenzenes is 74 percent. The catalyst shows no deactivation after 500 hours of continuous use.

What is claimed is:

1. A continuous flow process of alkylating benzene or substituted benzene comprising contacting the benzene or substituted benzene with an alkylating agent having from two to eighteen carbon atoms in the presence of a catalyst in a continuous flow reactor, the catalyst comprising an acidic mordenite zeolite having a silica/alumina molar ratio of at least 160:1 and a Symmetry Index above about 1.0, under conditions sufficient for the formation of an alkylated benzene or an alkylated substituted benzene, the catalyst being prepared by a method which comprises (i) calcining an acidic mordenite having a Symmetry Index between about 0.50 and about 1.3 and having a silica/alumina molar ratio less than 30:1 in air or heating the acidic mordenite in an inert atmosphere at a temperature in the range from about 300° C. to about 800° C., (ii) contacting the calcined or heated acidic mordenite with strong acid, and optionally (iii) repeating Steps (i) and (ii), to form an acidic mordenite having a silica/alumina molar ratio of at least 160:1 and having a Symmetry Index of at least about 1.

2. The process of claim 1 wherein the catalyst has a silica/alumina molar ratio of at least 175:1.

3. The process of claim 1 wherein the catalyst has a Symmetry Index of from 1 to about 2.

4. The process of claim 1 wherein the catalyst comprises an inert binder.

5. The process of claim 4 wherein the inert binder is silica binder.

6. The process of claim 1 wherein the alkylating agent is propylene.

7. The process of claim 1 wherein the alkylating agent is ethylene.

8. The process of claim 1 wherein the molar ratio of benzene or substituted benzene to alkylating agent is between about 1:1 and 10:1.

9. The process of claim 1 wherein the molar ratio of benzene or substituted benzene to alkylating agent is between about 1:1 and 3:1.

10. The process of claim 1 wherein a plurality of catalyst containing reaction zones in fluid connection in series is used, wherein the whole of the benzene or substituted benzene is delivered to a first reaction zone, and a series of fractions of alkylating agent are delivered respectively to the first reaction zone and between each pair of contiguous reaction zones.

11. The process of claim 10 wherein two to twenty catalyst containing reaction zones are used with a corresponding number of alkylating agent streams.

12. The process of claim 1 wherein the temperature is in the range from about 100° C. to about 300° C. during the alkylation.

13. The process of claim 1 wherein the pressure is in the range from about 10 bar to about 200 bar during the alkylation.

14. The process of claim 1 wherein benzene is contacted with ethylene or propylene as the alkylating agent.

15. The process of claim 1 wherein in Step (i) the temperature is in the range from about 500° C. to about 750° C., and wherein in Step (ii) the strong acid is an inorganic acid in aqueous acid solution having a concentration in the range from about 4N to about 12N, the ratio of the aqueous acid solution to acidic mordenite is in the range from about 3 cc aqueous acid solution per gram calcined or heated acidic mordenite to about 10 cc aqueous acid solution per gram calcined or heated acidic mordenite, the contacting occurring at a temperature in the range from about 22° C. to about 220° C.

16. A two catalyst bed process for producing monoalkylated benzene comprising:
   (A) contacting benzene or substituted benzene with an alkylating agent having from two to eighteen carbon atoms in the presence of a catalyst, the catalyst comprising an acidic mordenite zeolite having a silica/alumina molar ratio of at least 160:1 and a Symmetry Index above about 1.0, in a continuous flow reactor under temperature and pressure sufficient to maintain liquid conditions, the catalyst being prepared by a method which comprises
      (i) calcining an acidic mordenite having a Symmetry Index between about 0.50 and about 1.3 and having a silica/alumina molar ratio less than 30:1 in the presence of air or heating the acidic mordenite in an inert atmosphere at a temperature in the range from about 300° C. to about 800° C., and
      (ii) contacting the calcined or heated acidic mordenite with strong acid, and optionally
      (iii) repeating Steps (i) and (ii)
   to form an acidic mordenite having a silica/alumina molar ratio of at least 160:1 and having a Symmetry Index of at least about 1;
   (B) separating a polyalkylated benzene or a polyalkylated substituted benzene fraction from monoalkylated benzene or monoalkylated substituted benzene formed in Step A; and
   (C) contacting the polyalkylated benzene or polyalkylated substituted benzene fraction with benzene in the presence of an acidic mordenite catalyst having a silica/alumina molar ratio of at least 50:1 under conditions sufficient for the formation of monoalkylated benzene.

17. The process of claim 16 wherein the catalyst of step A has a silica/alumina molar ratio of at least 175:1.

18. The process of claim 16 wherein the catalyst of Step A has a Symmetry Index of from 1 to about 2.

19. The process of claim 16 wherein the catalyst of Step A comprises a silica binder.

20. The process of claim 16 wherein the alkylating agent is propylene.

21. The process of claim 16 wherein the alkylating agent is ethylene.

22. The process of claim 16 wherein the molar ratio of benzene or substituted benzene to alkylating agent is between about 1:1 and 10:1.

23. The process of claim 16 wherein the molar ratio of benzene or substituted benzene to alkylating agent is between about 1:1 and 3:1.

24. The process of claim 16 wherein in Step A a plurality of catalyst containing reaction zones in fluid connection in series is used, wherein the whole of the benzene or substituted benzene is delivered to a first reaction zone, and a series of fractions of alkylating agent are delivered respectively to the first reaction zone and between each pair of contiguous reaction zones.

25. The process of claim 24 wherein two to twenty catalyst containing reaction zones are used and a corresponding number of fractions of alkylating agent.

26. The process of claim 16 wherein the temperature in Step A is in the range from about 100° C. to about 300° C. in the alkylation.

27. The process of claim 16 wherein the pressure in Step A is in the range from about 10 bar to about 200 bar in the alkylation.

28. The process of claim 16 wherein the catalyst of Step C has a silica/alumina ratio of between about 50:1 and about 500:1.

29. The process of claim 16 wherein the catalyst of Step C has a Symmetry Index of at least 1.

30. The process of claim 16 wherein the catalyst of Step C has a Symmetry Index of between 1 and 2.

31. The process of claim 16 wherein the catalyst of Step C comprises a silica binder.

32. The process of claim 16 wherein in Step C the molar ratio of the total of benzene groups present in the benzene or substituted benzene and in the polyalkylated benzene fraction to the total of alkylated groups in the polyalkylated benzene is at least 1.5.

33. The process of claim 16 wherein the temperature in Step C is in the range from about 140° C. to about 300° C. and the pressure is sufficient to maintain liquid conditions.

34. The process of claim 16 wherein in Step C a polyisopropylated benzene fraction as the polyalkylated benzene fraction is contacted with benzene and the temperature is in the range from about 140° C. to about 250° C.

35. The process of claim 16 wherein in Step C a polyethylated benzene fraction as the polyalkylated benzene fraction is contacted with benzene and the temperature is in the range from about 200° C. to about 300° C.

36. The process of claim 16 wherein benzene is contacted with ethylene or propylene as the alkylating agent in Step A.

37. The process of claim 16 wherein in Step (i) the temperature is in the range from about 500° C. to about 750° C., and wherein in Step (ii) the strong acid is an inorganic acid in aqueous acid solution having a concentration in the range from about 4N to about 12N, the ratio of the aqueous acid solution to acidic mordenite is in the range from about 3 cc aqueous acid solution per gram calcined or heated acidic mordenite to about 10 cc aqueous acid solution per gram calcined or heated acidic mordenite, the contacting occurring at a temperature in the range from about 22° C. to about 220° C.

* * * * *